United States Patent [19]

Cipullo et al.

[11] Patent Number: 5,723,691
[45] Date of Patent: Mar. 3, 1998

[54] METHOD FOR PREPARING ION-EXCHANGE RESIN FOR USE AS A CATALYST IN THE SYNTHESIS OF BISPHENOLS

[75] Inventors: Michael John Cipullo, Prattville, Ala.; Eric James Pressman, Greenbush, N.Y.

[73] Assignee: General Electric Company, Pittsfield, Mass.

[21] Appl. No.: 522,187

[22] Filed: Aug. 31, 1995

[51] Int. Cl.$^6$ .............................. C07C 39/12; C07C 39/16
[52] U.S. Cl. ............................................. 568/727; 568/723
[58] Field of Search ................................... 568/723, 727; 521/25; 502/159

[56] References Cited

U.S. PATENT DOCUMENTS 3,037,052  5/1962  Bortnick.
5,146,007  9/1992  Cipullo.

*Primary Examiner*—Gary Geist
*Assistant Examiner*—Karl J. Puttlitz, Jr.

[57] ABSTRACT

In the preparation of bisphenol-A by condensation of phenol with acetone in the presence of an acidic ion-exchange resin catalyst, pretreatment of the catalyst to render it free of acidic oligomers which are detrimental to the preparation of bisphenol-A entails washing the catalyst resin with deionized water until the washings show a specific conductance of less than 50 micromho/cm at 25° C.

8 Claims, No Drawings

METHOD FOR PREPARING ION-EXCHANGE RESIN FOR USE AS A CATALYST IN THE SYNTHESIS OF BISPHENOLS

BACKGROUND OF THE INVENTION

1. Field of the Invention

The invention relates to processes for the synthesis of dihydric phenols and more particularly to a process for preparing bisphenol-A.

2. Brief Description of Related Art

The dihydric phenol 2,2 bis(4-hydroxyphenyl) propane (commonly referred to as "bisphenol-A") is commercially prepared by condensing 2 moles of phenol with a mole of acetone in the presence of an acid catalyst. A mole of water co-product is co-produced.

A catalyst utilized in the commercial processes is a macro-reticular or gelular, acidic ion-exchange resin; see for example the U.S. Pat. No. 4,191,843 (Kwantes et al). These catalysts are the product of monoethylenically unsaturated monomers copolymerized with polyvinylidene monomers, as described for example in the U.S. Pat. No. 3,037,052 (Bortnick). Preferred macro-reticular resins are sulfonated to position sulfonic acid groups, pendant from the aromatic nucleus of the vinylidene moiety; see the U.S. Pat. No. 3,037,052.

The above-described acid catalyst (sulfocationites) contains up to 40 to 85 percent by weight of water and may be made available by the manufacturer in this hydrated state. The presence of the water will inhibit the desired catalyst activity in condensing phenol with acetone, because the water will bind to the sulfonic acid groups in competition with reactant. For this reason, Bortnick (U.S. Pat. No. 3,037,052) teaches one to dehydrate the catalyst prior to use. As a method of dehydration, Bortnick suggests "drying at 105° C. to about 125° C. at a pressure of 5 to 10 mm" or by azeotropic distillation with an organic liquid (column 4, lines 54–64).

Kwantes et al., in the U.S. Pat. No. 4,191,843 describing in particular the preparation of bisphenols, states that "the reactor may be filled with the acid ion exchanger by any known technique. Such techniques include adding the desired amount of dry ion exchanger, water wet ion exchanger or slurry of the ion exchanger in the reactor"; see column 2, lines 51–55. Details of the drying procedure are not elaborated upon beyond stating that the reactor charged resin is "drained"; see the patent Example 1.

In the commercially practiced processes for preparing bisphenol-A, acid ion-exchange resins are dried in the plant reactor (usually a column reactor) prior to initiation of the reaction between phenol and acetone. Drying is effected by passing phenol over the catalyst in the absence of acetone, to absorb and/or displace the water associated with the acid ion-exchange resin. Water that is absorbed or displaced by the phenol is removed from the resin bed as an effluent stream. The water is ultimately removed from the phenol effluent by employing conventional separation techniques such as distillation and extraction. Water removal causes a reduction of volume of the resin bed so that more resin can be subsequently added to the bed. The alternating steps of dehydration and resin addition are continued until the reactor is completely charged with a dehydrated resin. Then the desired condensation reaction is initiated.

The aforementioned dehydration procedure is time consuming, often requiring several weeks and results in substantial reactor down time. Where a plant utilizes large amounts of catalyst resin, resin addition and drying can take several months. Furthermore, cycles of resin addition and dehydration are known to stress and damage macro-reticular or gelular resin beads. This deleteriously affects reaction mixture flow in the reactor and pressure drop across the bed.

One solution considered for the problems associated with the commercially practiced procedure of drying the acidic ion-exchange resin is to follow the teachings of the aforementioned U.S. Pat. No. 3,037,052 and pre-dry the resin to an anhydrous state before it is charged to the column reactor. However, this procedure also has certain disadvantages. For example, if the resin is not rapidly dried under elevated temperature conditions (circa 150° C.), Zundel et al. has reported (Physik. Chem. (Frankfurt) 59, 225 [1968]) that the water is hydrogen bonded to three sulfonic acid groups and cannot be removed even under severe drying conditions. However, if drying is carried out at too rapid a rate, the resin beads may be subjected to abrasion and damage with a resultant loss of operating life. Clearly, the rate of drying is critical to an economic process.

Another solution is described in U.S. Pat. No. 5,146,007 (Cipullo) wherein the ion-exchange resin is partially dried (20–90% of the water removed) before it is loaded into the reactor. This is more efficient, reducing the number of steps and saving weeks of catalyst preparation time. Then dehydration is completed with the known and practiced procedure of water absorption/displacement from the resin with phenol. Resin volume changes are held to a minimum, thereby avoiding resin degradation. Advantageously, the total time required in a commercial plant for charging and drying the resin is substantially reduced.

Although the method of U.S. Pat. No. 5,146,007 (Cipullo) effectively removes water from the ion exchange resin, rendering it active, significant amounts of water soluble acids and resin manufacturing by-products are left in the resin. These residual materials cause problems for a period of time after the resin is placed in service, and can result in bisphenol-A product that is thermally unstable and has elevated color. The process of the present invention addresses this problem of catalyst contamination, and can be used in the pre-treatment of the catalyst before it is dehydrated by the method of U.S. Pat. No. 5,146,007, which is incorporated herein by reference thereto. When this is done, the bisphenol-A product has improved color and thermal stability.

SUMMARY OF THE INVENTION

The invention comprises a process for preparing a hydrated, acidic ion-exchange resin catalyst for catalyzing the condensation of a phenol with a ketone, which comprises;

washing the catalyst with deionized water until the water washings exhibit a specific conductance of less than about 50 micromho/cm at 25°; and then dehydrating the washed ion-exchange resin.

In a continuous process, the specific conductance of the washings can be measured using a conductance sensor positioned to analyze the washings as they flow through and from the resin bed.

DETAILED DESCRIPTION OF THE PREFERRED EMBODIMENTS OF THE INVENTION

Acidic ion-exchange resins useful to catalyze the condensation of phenols with ketones are generally well known compositions as are methods of their preparation; see for example the preparative procedures described in U.S. Pat. No. 3,037,052 which is hereby incorporated herein by reference thereto. Representative of acid ion-exchange resins are strong-acid ion exchangers, such as those resins or polymers having a plurality of pendant sulfonic acid groups. Examples include sulphonated polystyrene or poly(styrene-divinylbenzene) copolymer and sulphonated phenol-formaldehyde resins. The sulphonated resins are commercially available in water swollen form as gellular, micro-recticular and macro-recticular types. Specific examples of suitable resins are Amberlite IR-120H, Amberlyst 15H, Amberlyst 31 and 131 Dowex 50-X-4, Dowex MSC-1H, Duolite c-26, Permutit QH, Chempro C-2, Purolite CT-124, Bayer K-1221 and Imac C8P/H (Amberlite, Amberlyst, Dowex, Duolite, Purolite, Permutit, Chempro and Imac are registered U.S. Trademarks). Further examples of such ion exchangers as well as methods for preparing such ion exchangers are described in the Encyclopedia of Polymer Science and Technology, 1967, vol. 7, pages 695 to 708. The exchange capacity of the acidic resin is preferably at least 2.0 meq. $H^+$/g of dry resin, with exchange capacities in the range of from 3.0 to 5.5 meq. $H^+$/g (dry resin) particularly preferred. One preferred catalyst used in the process of the present invention is the Amberlyst® gelular types, which are styrene cross-linked with divinylbenzene or like cross-linking monomer and having pendant sulfonic acid groups attached to the aromatic nucleus of the styrene moiety. Sulfonation may be by the process described in U.S. Pat. No. 2,366,007 which is incorporated herein by reference thereto.

Prior to their use to catalyze the condensation of phenols with ketones according to the present process and prior to dehydration of the ion-exchange resins as received from their manufacturers, the ion-exchange resins are treated in accordance with the present invention to remove residual catalyst manufacturing by-products and any additional materials which may form immediately after manufacture and arising from natural decomposition of the resin. The treatment comprises washing the hydrated catalyst with deionized water (with a specific conductance of less than about 50 micromho/cm at 25° C.) until the effluent of washings yield water with a similar specific conductance as a measure of decontamination of the resin. In some instances, it may be found that the specific conductance of the water hydrating the catalyst resin is, before treatment according to the invention, at a value already below 50 micromho/cm at 25° C. The process of the invention is also advantageous in these instances, reducing further the specific conductance. In general, the lower the specific conductance, the better will be the product bisphenol in terms of color and thermal stability. Even a 10 percent reduction in the specific conductance of the water washings is advantageously reflected in the product bisphenol. For this reason, specific conductance values of less than about 15 micromho/cm are preferred.

The washing with deionized water is advantageously carried out at a temperature within the range of from about 0° C. to 80° C., preferably above room temperatures. Since the measurement of specific conductance is temperature dependent, its measurement at a temperature above or below 25° C. must be corrected for as those skilled in the art will appreciate.

Following decontamination with water washing, the ion-exchange resin may be dehydrated by any conventional method known in the art. Preferably, the resin is dehydrated by the method of Cipullo as described in the U.S. Pat. No. 5,146,007. In general, the method is as follows.

Advantageously, catalyst drying is carried out by first heating the water saturated catalyst to vaporize the water, entrain the vapors in a moving gas (air, inert gas such as nitrogen) or under vacuum and separate a portion of the vapors from the catalyst. The weight proportion of water vaporized and removed from the catalyst can vary, but the preferred amount of water remaining in the catalyst is generally within the range of from 2 to 50 percent.

In the process of Cipullo, the resin catalyst is not rendered anhydrous by the initial drying through vaporization of the water content. Removal of the water content shrinks the resin volume and potentially degrades resin structure. Reducing the water content partially, preferably to the point where the catalyst resin volume is near (plus or minus about 25 percent by volume) that of the phenol saturated resin volume, is advantageous. For example, reducing the water content of a given 60 percent (by weight) water resin to a level of from 20 to 40 percent provides a resin occupying a volume approximately equal to the same resin saturated with phenol (appreciate that the solvent-retention capacity of an acidic ion-exchanger is a reproducible equilibrium quantity dependent upon ion-exchange capacity, ionic form, the solvent, the degree of cross-linking, temperature, humidity and other variables; see for example Helfferich, Ion Exchange, McGraw-Hill Book Co., Inc., New York, N.Y. [1962], Chapter 5). Thus, passing phenol through a reactor containing this particular resin (initially with 20 to 40 weight percent of water will not significantly affect the resin volume, thereby minimizing degradation resulting from stresses during drying and shrinking.

The partially dehydrated catalyst may be charged to an appropriate reactor, for example a fixed bed column reactor and saturated with phenol to complete dehydration. Alternatively, the wet ion exchange resin may be charged to the reaction zone and subjected to partial drying as described above in-situ, before saturation with phenol. The phenol addition may be carried out in the reactor or in a different vessel and then transferred to the reactor or reaction zone. The catalyst is further dried by the addition of phenol to the desired level of water content in the catalyst. This level of water will affect the rate of reaction between the phenols and ketones. Essentially about 4 weight percent water in the phenol effluent would bring about a marginally acceptable reaction rate while a level of about 2 weight percent in the effluent or less is preferred. A level of less than about 1 weight percent is most preferred. The reaction zone is then ready to receive the ketone reactant and a molar excess of the phenol reactant for condensation following known procedures.

The reaction zone may comprise a single reactor or two or more reactors in series or in parallel. In the case of a multi-reactor reaction zone, suitably all of the phenol is fed to the first reactor and the ketone compound is either fed all to the first reactor or divided between the first and second and possibly further reactors.

The molar ratio of phenol to ketone is at least 2 to 1 with a stoichiometric excess of phenol being preferred. Molar ratios are preferably from 3:1 to 40:1, with molar ratios of from 10:1 to 30:1 being most preferred. The optimum ratio depends on reaction conditions, e.g., temperature of reaction and desired conversion.

The reaction temperature in the reactor zone may vary from 40° C. to 95° C. with reaction temperatures in the range of from 55° C. to 90° C. being preferred.

The reaction time in the reactor zone may also vary and depends on reaction temperature. For example, the liquid hour space velocity (LHSV) of the feed may vary between wide limits with velocities in the range of from 0.2 to 40 liters feedstream/(liter catalyst/hour).

The following preparations and examples describe the manner and process of making and using the invention and set forth the best mode contemplated by the inventors for carrying out the invention.

Comparative Preparation (Not of the Invention)

A quantity of a gelular acidic ion exchange resin of the sulfonated type (Amberlyst 31, Rohm and Haas Company) having a water content of 60 percent by weight is partially dehydrated in a drying oven to a water content of about 20.6 percent.

A tubular reactor is charged with a quantity of resin as prepared above and dried further by passing phenol over the resin bed. When test samples show the phenol effluent has less than 1% water, a feedstream comprising phenol and acetone (mole ratio 8:1) is eluted through the reactor at a liquid hour space velocity of 2.6 liters/(liter catalyst/hour)at a temperature of 70° C. and the reaction zone effluent continuously withdrawn and fed to a purification system for separation of the product bisphenol-A. The product, upon analysis, showed 1030 ppm of 3-mercaptopropionic acid, 48.3 percent conversion to pp'-bisphenol-A, 89.78% pp' selectivity and 2.1 ppm water-soluble oligomeric acids (@ 42–45 hrs.).

EXAMPLE 1

Following the general procedure of the *Comparative Preparation*, supra., but replacing the resin as used therein with the same resin prewashed with deionized water in a C frit funnel, and partially dried to a water content of 21.6 percent, a product bisphenol-A was obtained, which upon analysis showed 997 ppm of 3-mercaptopropionic acid, 51.0 percent conversion to pp'-bisphenol-A, 89.83 percent pp' selectivity and 1.23 ppm oligomers (@46–48 hrs.).

Samples of the washed (Example 1) and the unwashed (Preparation) resin, upon analysis showed the following test results:

|  | Unwashed Resin | Prewashed Resin |
| --- | --- | --- |
| partially dried water content: | 20.6% | 21.6% |
| conductivity (milli MHO)[1] | 15.8 | 3.2 |
| Color[2] | 0.502 | 0.04 |
| Tar Factor[3] | 2.79 | 0.36 |
| ppm oligomer[4] | >100 | 33.1 |

Footnotes:
1-Determined by adding sufficient deionized water to make a 3/1 (wt/wt) water/partially dried catalyst slurry, shaking for 15 minutes in a glass bottle, followed by separation of the resin from the solution and measurement of the conductivity of the solution.
2-Determined by measuring the absorbance of the aqueous solution from (1 above) following a 20x dilution with deionized water at 350 NM in a 1 cm cell.
3-Determined by eluting 50–60 ml of purified phenol through 6.45 g of catalyst (dry basis) at 70° C., WHSV = 2.6. Methanolic solution of the effluent (0.500 g in 50 ml methanol) was used to determine tar factor (absorbance at 350*50/gr of sample).
4-Determined by potentiometric titration of the phenolic solution obtained in (3 above) using tetrabutyl ammonium hydroxide.

This shows both resins worked well as reaction catalysts, exhibiting similar activity and selectivity in reaction. Prewashing of the catalyst resin with water helped maintain a lower acid oligomer elution long after initiating the bisphenol-A reaction with the resin. Previous work has shown that these acidic oligomers are detrimental to product quality when they reach downstream high temperature operations in the manufacturing process.

For comparison purposes, the above results are tabulated as follows:

|  | Unwashed | Prewashed |
| --- | --- | --- |
| ppm 3-mercaptopropionic acid | 1030 | 997 |
| % conversion to pp'-BPA | 48.3 | 51.0 |
| % pp' selectivity | 89.78 | 89.83 |
| ppm oligomers | 2.1 | 1.23 |
|  | (@ 42–45 hrs) | (@ 46–48 hrs) |

What is claimed is:

1. An improved process for preparing a hydrated, acidic ion-exchange resin catalyst, with low color and a low tar factor, for catalyzing the condensation of a phenol with a ketone, which comprises:

washing the catalyst; and then dehydrating the washed ion-exchange resin wherein the improvement comprises washing with deionized water until the water washings exhibit a specific conductance of less than about 50 micromho/cm at 25° C.

whereby the color of the resin is no more than 0.04 and the tar factor is no more than 0.4.

2. The process of claim 1 wherein the washing is carried out at a temperature within the range of from about 0° C. to about 80° C.

3. The process of claim 1 wherein the ion-exchange resin is gelular.

4. An improved process for the preparation of bisphenol-A which comprises:

providing a hydrated acidic ion-exchange resin catalyst for catalyzing the condensation of phenol with acetone;

washing the provided resin catalyst;

vaporing a portion of the water associated with the hydrated catalyst;

separating sufficient of the water vapor from the catalyst to remove from 25 to 95 percent by weight of said water, whereby a partially dehydrated catalyst is obtained;

contacting the partially dehydrated catalyst with phenol so as to remove additional water from the catalyst until the water content of the effluent phenol contains less than about 4 weight percent water; and condensing phenol and acetone in a reaction zone at a temperature within the range of from 40° to 95 ° C., in the presence of the dehydrated catalyst wherein the improvement comprises washing with deionized water until the water washings exhibit a specific conductance of less than about 50 micromho/cm at 25° C.

whereby the ppm of oligomers is reduced by about 40%.

5. The process of claim 1 wherein the specific conductance is less than about 15 micromho/cm.

6. The process of claim 2 wherein the specific conductance is less than about 15 micromho/cm.

7. The process of claim 4 wherein the washing is carried out at a temperature within the range of about 0° C. to about 80° C.

8. The process of claim 4 wherein the specific conductance is less than about 15 micromho/cm.

* * * * *